US00PP11682P

United States Patent [19]

Kent

[11] Patent Number: Plant 11,682

[45] Date of Patent: Dec. 12, 2000

[54] BROMELIAD PLANT NAMED 'GUZ 202'

[75] Inventor: Jeffrey C. Kent, Vista, Calif.

[73] Assignee: Kent's Bromeliad Nursery, Inc., Vista, Calif.

[21] Appl. No.: 09/114,412

[22] Filed: Jul. 13, 1998

[51] Int. Cl.[7] ..... A01H 5/00

[52] U.S. Cl. ..... Plt./371

[58] Field of Search ..... Plt./371

[56] References Cited

U.S. PATENT DOCUMENTS

P.P. 9,045 1/1995 Kent ..... Plt./371

P.P. 10,369 4/1998 Bak et al. ..... Plt./371

*Primary Examiner*—Bruce R. Campell
*Assistant Examiner*—Wendy A. Baker
*Attorney, Agent, or Firm*—James A. Lucas; Driggs, Lucas, Brubaker & Hogg Co., L.P.A.

[57] ABSTRACT

A pink bromelaid hybrid has an almost rose-like appearance due to the closeness of the scape bracts, and consistent rose pink coloration from base to apex, surrounding the floral bracts which are translucent and colorless at the base and the apex, blending into a more intense pink color in the middle. The overlapping effect of the bracts is white.

1 Drawing Sheet

BACKGROUND OF THE INVENTION

This application relates to a newly developed interspecific hybrid Guzmania plant resulting from a planned breeding program that I conduct on an ongoing basis. The objects of the breeding program include the crossing of selected parent plants from the numerous, compatible species within the genus, to obtain plants with novel and attractive phenotypes, coloration, and flowering forms. Other important selection factors may include ultimate plant size and shape, disease resistance, tolerance to different soil and growing conditions and vigor.

Among the objects of my program are to produce plants which will be attractive to the consumer; which will develop reasonably rapidly under controlled conditions; and, retain for a long term, highly attractive and bright inflorescence; i.e., bract coloration, after being induced into the flowering stage. It is a specific object to provide a low maintenance plant which will be a long term decorative appointment offering an exotic color splash in the home of a buyer, or to serve as a substitute for flowering plants which have a shorter flowering duration in, for example, indoor plant and flower scapes. Finally, it is an object to develop plants which may be easily and efficiently multiplied by state-of-the-art tissue culture methods while continuing the distinctive characteristics of the plants through progressive clonal generations.

The plant of this disclosure was a selection from the progeny resulting from the cross of *Guzmania lingulata* 'Panama Orange' (unpatented)×*Guzmania wittmackii*, 'Light Pink Equador' (unpatented). With the recognition that this seedling from the cross satisfied the objects of the breeding program, the individual was isolated and set aside for further observation and testing. The resulting selection has been assigned the designation 'GUZ 202' for purposes of identification. This plant has been reproduced by tissue culture at Evergem Belgium, and elsewhere, and the clonal specimens resulting have been determined to be identical to the original selection in all distinguishing characteristics. The superior attributes of this plant will be revealed in the botanical descriptions to follow.

SUMMARY OF THE INVENTION

The attributes of the plant 'GUZ 202' which distinguish it from the other similar Guzmania hybrids are described as follows:

The inflorescence has an appearance almost of a rose flower due to the closeness of the scape bracts and the consistent rose pink color of the scape bracts, obverse and reverse, from base to apex. The floral bracts are pink in color and fade slightly towards a more translucent color at the apex. The overlapping effect of the bracts is white. Unlike other pink Guzmania of basically the same form, GUZ 202 satisfies the need for a rose pink, rather than a purple pink effect.

The plant contains medium leaves having a length of 17" (42 cm) and a width of 2" (5.1 cm). The leaves are arching and somewhat drooping, smooth and with a smooth margin. The leaves are medium dark color obverse and reverse with some coral staining and lineation extending from the base about ⅓ of the length of the leaves.

This sterile hybrid is attractive because the scape bracts are consistent in color, base to apex. The bracts are a light to medium rose pink, not a purple pink in color, unlike most of the other pink Bromeliad hybrids. The scape bracts are fairly close together giving an almost rose flower-like apperance to the whole in florescence. This hybrid holds its color well in dim interior conditions for up to two and one half months.

BRIEF DESCRIPTION OF THE DRAWING

The single color photograph of the drawing depicts a mature specimen of the plant in mid to late flowering stage. Illustrated are the mature leaves, scape bract and floral bract. The color definitions in the specification have been taken from The R.H.S. Colour Chart of The Royal Horticulture Society. While the colors depicted are believed to be of a high level of color fidelity, the coloration of this plant should be understood to be approximate, and somewhat variable as a function of cultural conditions and horticultural practices. For example, the bract color might slightly fade if the plant is subjected to bright light and the leaf color may vary depending on the composition and the concentration of fertilizer which may be applied to the plant. The colors depicted are as close to the actual coloration of the plant as is possible to attain in a photographic illustration of this quality, however due to factors such as light reflectance, minor differences in coloration may appear.

It takes approximately a one year time period from liner to market. No unusual susceptibility to diseases of Guzmania has been noted prior to market.

BOTANICAL DESCRIPTION OF THE PLANT

Parentage:

*Seed parent.*—*Guzmania lingulata* 'Panama Orange'.

*Pollen parent.*—*Guzmania wittmackii* 'Light Pink Equador'

Propagation:

*Method of asexual reproduction.*—Tissue culture.

*Where reproduction took place.*—Reginald De Roose BVBA Droogte 139, B9940 Evergem, Belgium.

Plant: Monocot Perennial. Medium in size.

*Overall height from soil surface including inflorescence*—18" to 20".

*Overall width.*—25" to 27".

Upright, spreading and drooping. Dense. Vase formed.

*Hardiness at temperatures below* 23° F. — Tender.

Leaves:

*Length.*—17";

*Width.*—2";

*Number.*—27–29.

Medium in size Lanceolate, narrowly acuminate leaves arching, somewhat dropping, 141-B in color obverse and reverse, Some staining and lineation 67-B From the base about ⅓ up the stem obverse and reverse Medium thickness Medium light color Smooth Margin— Smooth Inflorescence a branched spike

*Scape length.*—14"–16".

*Bracts.*—Number 12–14;

*Shape.*—lanceolate, terminating in a long acuminate tip;

*Bract base.*—Truncate;

*Bract tip.*—Narrow acute.

*Scape bracts.*—6½"×1⅜" at base. 3½" at apex, Obverse and reverse clasping stem. Lower bracts 66-C in color from base approximately ⅓ of the distance towards the tip; remainder of bract 141-B in color, with some tipped 66-C in color; upper bracts becoming all 66-C in color.

*Floral bracts.*—2¾"×⅝". 66B at the base becoming slightly translucent and fading to 66C at apex with bracts overlapping.

*Scape length.*—14"–16".

Flower buds:

*Hardiness at temperatures below* 32° F.—Tender.

Medium in size Long in length — size and length are compared to typical bud size for the species 1" (2.5 cm.)×¼ (0.63 cm.) just before expansion to anthesis. Pointed and appressed.

*Color.*—155D.

Flowers: Morphology as for Guzmania Flowers Apetiolate Medium in size Sepals 1¼"×3/16" translucent in color; 3 in number. Petals 1½"×114" translucent; scarcely open at anthesis 3 in number; petals jouned ⅓ length up from base.

*Corolla.*—Cylindrical.

Fruit: A three celled capsule splitting longitudinally when mature, Seeds with pappus-seeds not viable.

What is claimed is:

1. A new and distinct variety of Guzmania plant named 'Guz 202', as illustrated and described, characterized by consistent rose pink color of scape bracts from base to apex, the closeness of said bracts giving almost a rose flower appearance to the inflorescence.

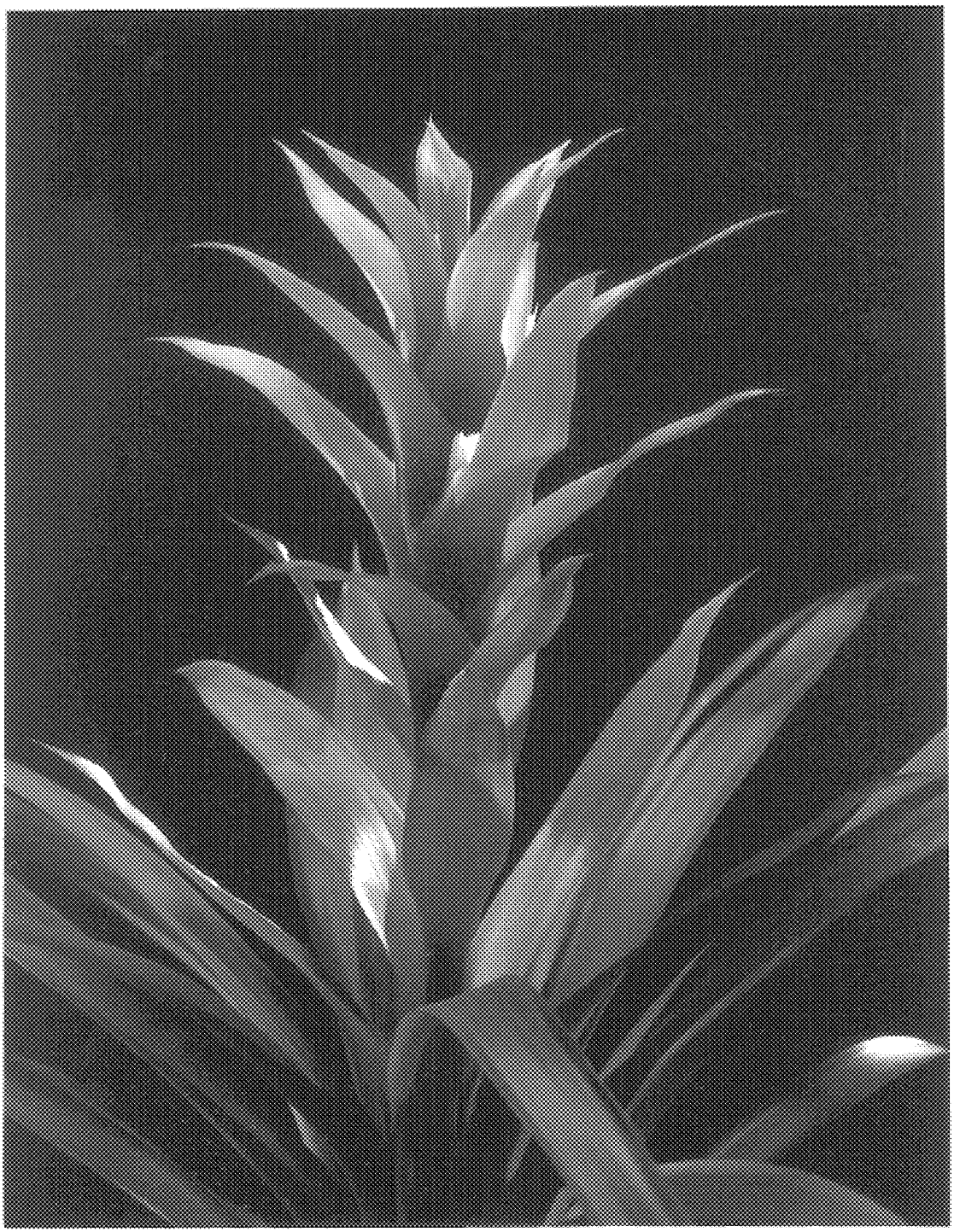

* * * * *